US008936628B2

(12) United States Patent
Anderson

(10) Patent No.: US 8,936,628 B2
(45) Date of Patent: Jan. 20, 2015

(54) SUTURE-RETAINING STERNAL CLAMP ASSEMBLY

(75) Inventor: Charles Anderson, Gig Harbor, WA (US)

(73) Assignee: KLS-Martin, L.P., Jacksonville, FL (US)

(*) Notice: Subject to any disclaimer, the term of this patent is extended or adjusted under 35 U.S.C. 154(b) by 716 days.

(21) Appl. No.: 12/806,612

(22) Filed: Aug. 17, 2010

(65) Prior Publication Data

US 2011/0054547 A1 Mar. 3, 2011

Related U.S. Application Data

(60) Provisional application No. 61/274,420, filed on Aug. 17, 2009.

(51) Int. Cl.
*A61B 17/84* (2006.01)
*A61B 17/04* (2006.01)
*A61B 17/82* (2006.01)
*A61B 17/06* (2006.01)

(52) U.S. Cl.
CPC .......... *A61B 17/0401* (2013.01); *A61B 17/823* (2013.01); *A61B 17/842* (2013.01); *A61B 17/06061* (2013.01)
USPC .............. 606/324; 606/233; 606/216; 606/74

(58) Field of Classification Search
USPC ........... 606/324, 300, 151–158, 74, 250, 251, 606/252, 253, 263, 282, 321, 105, 606/232–233; 24/527; 623/13.13, 13.14; 70/14, 16, 18, 19, 208; 224/448, 456, 224/461, 536, 558, 570; 269/143, 249; 29/276; 294/34, 168, 119.1
See application file for complete search history.

(56) References Cited

U.S. PATENT DOCUMENTS

| | | | | |
|---|---|---|---|---|
| 815,264 | A * | 3/1906 | Chambers | 606/233 |
| 3,014,483 | A * | 12/1961 | McCarthy | 606/233 |
| 3,625,220 | A * | 12/1971 | Engelsher | 606/233 |
| 3,695,271 | A * | 10/1972 | Chodorow | 606/233 |
| 3,831,608 | A * | 8/1974 | Kletschka et al. | 606/233 |
| 4,201,215 | A * | 5/1980 | Crossett et al. | 606/216 |
| 4,275,736 | A * | 6/1981 | Chodorow et al. | 606/233 |
| 4,512,346 | A | 4/1985 | Lemole | |
| 4,583,541 | A | 4/1986 | Barry | |
| 4,813,416 | A | 3/1989 | Pollak et al. | |
| 4,896,668 | A | 1/1990 | Popoff et al. | |
| 5,139,498 | A | 8/1992 | Ley | |
| 5,352,225 | A * | 10/1994 | Yuan et al. | 606/324 |
| 5,571,109 | A * | 11/1996 | Bertagnoli | 606/86 A |
| 6,030,410 | A | 2/2000 | Zurbrugg | |
| 6,051,007 | A | 4/2000 | Hogendijk et al. | |
| 6,066,141 | A * | 5/2000 | Dall et al. | 606/74 |
| 6,287,307 | B1 * | 9/2001 | Abboudi | 606/54 |
| 7,033,377 | B2 * | 4/2006 | Miller, III | 606/324 |
| 7,670,367 | B1 * | 3/2010 | Chouinard et al. | 623/1.15 |

* cited by examiner

*Primary Examiner* — Todd Manahan
*Assistant Examiner* — Marcela I Shirsat
(74) *Attorney, Agent, or Firm* — Thomas C. Saitta

(57) ABSTRACT

A sternal clamp having a first sliding body member and a second sliding body member telescopically mated, and a suture-receiving channel disposed on the exterior of the first sliding body member and the second sliding body member, wherein the first sliding body member and the second sliding body member are securable about a severed sternum by encircling and securing a suture about the first sliding body member and the second sliding body member, the suture being received and retained within the suture-receiving channel.

16 Claims, 2 Drawing Sheets ed and divided in surgery. The sternal clamp comprises a
SUTURE-RETAINING STERNAL CLAMP ASSEMBLY This application claims the benefit of U.S. Provisional Patent Application Ser. No. 61/274,420, filed Aug. 17, 2009.

BACKGROUND OF THE INVENTION

This invention relates generally to the field of medical devices, more particularly surgical sternal clamps.

A sternal clamp is a device that is used to secure two lateral halves of a sternum that has been longitudinally severed and divided in surgery, such as is often required to provide access to the interior of the chest cavity. The sternal clamp comprises a pair of sliding or telescoping clamp members, with each paired clamp member having means to grasp or abut the exterior edge of the sternum, such as a single or multiple leg or hook members extending to the rear of the clamp member. The sternal clamp device is positioned across the sternum with the hook members positioned between adjacent ribs. The two clamp members are then compressed, i.e., moved toward each other in sliding fashion, to shorten the device and thereby pull the sternal halves together. The clamp members are then locked or secured in this contracted position by various mechanical means.

A problem with the known devices is that the locking mechanisms utilized to maintain the sternal clamp in the compressed or contracted position are typically cumbersome, difficult to adjust and difficult to remove. Some mechanisms are not releasable at all once the clamp has been compressed. Some mechanisms do not allow the clamp members to be extended once the device has been compressed. Some mechanisms require the use of screws or similar fasteners that can be dropped or lost by the surgeon during the clamping step. All of these problems are exacerbated in emergency situations where immediate removal of the sternal clamp is required, such that in many cases destruction of the clamp by sawing or the like is the only suitable method for rapid access.

It is an object of this invention to provide a sternal clamp device that satisfactorily addresses the problems set forth above. It is a further object to provide such a device that provides a simple and straightforward mechanism for securing the clamp in the closed or compressed position, as well as providing a mechanism that can be quickly and easily released.

SUMMARY OF THE INVENTION

The sternal clamp assembly comprises in combination a first sliding body member and a second sliding body member, both adapted to receive and retain a securing cable. The first and second sliding body members mate in a sliding, telescoping manner along a longitudinal axis such that the device may be lengthened or shortened by relative movement of the sliding body members. Each sliding body member comprises an interconnecting bridging portion and means for abutting the lateral sides of a sternum, such as a projection member comprising a leg and foot portion. A suture-receiving channel is provided on at least a portion of the outer surface of each sliding body member, the channel adapted to receive the suture in a manner whereby the suture can be wrapped around the sternum and the clamp, tightened to pull the two sliding body members together snuggly against the sternum, and then tied or otherwise secured such that the sliding body members are precluded from separating unless and until the suture is released or cut. Preferably, the sliding body members are also provided with anchoring channels extending to the sides of the sliding body members and in communication with the suture-receiving channel, thus providing shoulders or cleats to facilitate securement of the suture.

DETAILED DESCRIPTION OF THE INVENTION

Figure 1:
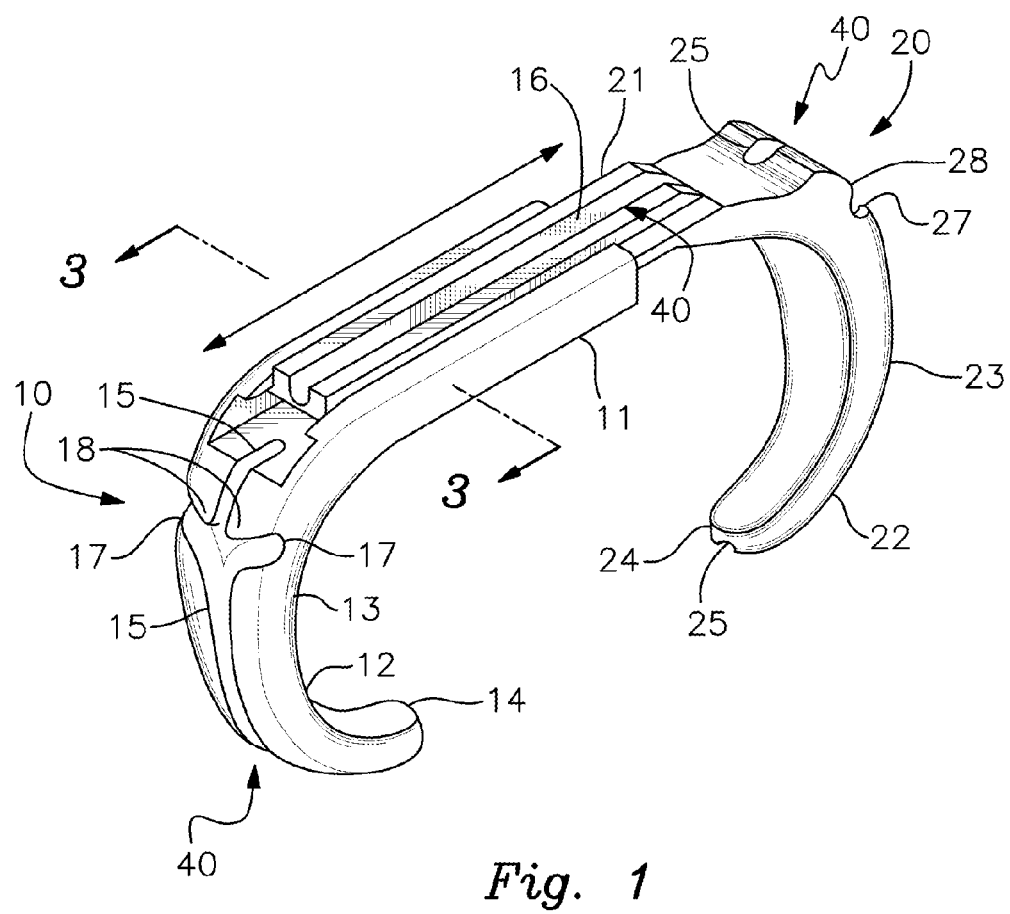
FIG. 1 is a perspective view of an embodiment of the invention.

With reference to the drawings, the invention will now be described in detail with regard for the best mode and the preferred embodiment. In a most general sense, the invention is a sternal clamp device or assembly adapted to secure two lateral halves of a sternum that has been longitudinally severed and divided in surgery. The sternal clamp comprises a pair of sliding or telescoping clamp members, with each paired clamp member having means to grasp or abut the exterior edge of the sternum, such as a single or multiple leg or hook members extending to the rear of the clamp member. The sternal clamp device is positioned across the sternum with the hook members positioned between adjacent ribs. The two clamp members are then compressed, i.e., moved toward each other in sliding fashion, to shorten the device and thereby push the sternal halves together. The clamp members are then locked or secured in this contracted position to retain the sternal halves in abutting relation.

The suture-receiving sternal clamp comprises a first sliding body member 10 and a second sliding body member 20 that are cooperatively mated in sliding, telescoping manner such that the overall longitudinal dimension of the clamp can be lengthened or shortened by relative movement of the two sliding body members 10/20. In the embodiment shown in the drawings, the second sliding body member 20 comprises an interconnecting bridging portion 21 that is received by an interconnecting bridging portion 11 of the first sliding body member 10, with the bridging portion 21 comprising a pair of laterally extending rails 31 that are received within elongated slots 32 formed in walls 33 of bridging portion 11. The first and second sliding body members 10/20 are free sliding in either direction.

The first sliding body member 10 further comprises a generally J-shaped projection member 12 extending substantially perpendicularly to the bridging portion 11, with the projection member 12 comprising a leg portion 13 and an in-turned foot portion 14. Likewise, the second sliding body member 20 further comprises a generally J-shaped projection member 22 extending substantially perpendicularly to the bridging portion 21, with the projection member 22 comprising a leg portion 23 and an in-turned foot portion 24. Leg portions 13/23 are adapted to abut the lateral edges of the sternum when in use, with foot portions 14/24 adapted to be positioned to the rear of the sternum in use. In other embodiments, a pair of projections members 12/22 may be provided on each sliding body member 10/20, in which case the clamp is positioned such that the paired projections 12 and the paired projections 22 are positioned on the sternum so as to bracket opposing ribs.

A circumferential suture-receiving channel is provided on the exterior side of the sternal clamp, suitably sized so as to receive and retain a suture, wire-suture, wire, cable or a like member 30, the suture-receiving channel being aligned in the longitudinal direction of the clamp, i.e., transverse to the longitudinal direction of the sternum when the clamp is in use. The suture-receiving channel comprises at least projection channels 15/25 disposed on the exterior side of projection members 12/22, and preferably also comprises a bridging channel 16 disposed on the exterior side of the bridging portion 21.

With this structure, the sternal clamp may be extended and positioned transversely across a sternum that has been severed into two longitudinal halves. The suture 30 is then passed behind the sternum and seated into the projection channels 15/25 with free ends of the suture 30 exposed. The suture 30 is then crossed and cinched to force the sliding body members 10/20 together such that the leg portions 13/23 press the sternal halves together. The suture 30 is then seated into the bridging channel 16 and knotted, twisted or otherwise secured such that the sliding body members 10/20 are locked into the compressed position. In the event that the sternal halves need to be re-opened to access the internal organs, the clamp is quickly released simply by severing or releasing the suture 30 and spreading the sliding body members 10/20.

Figure 2:
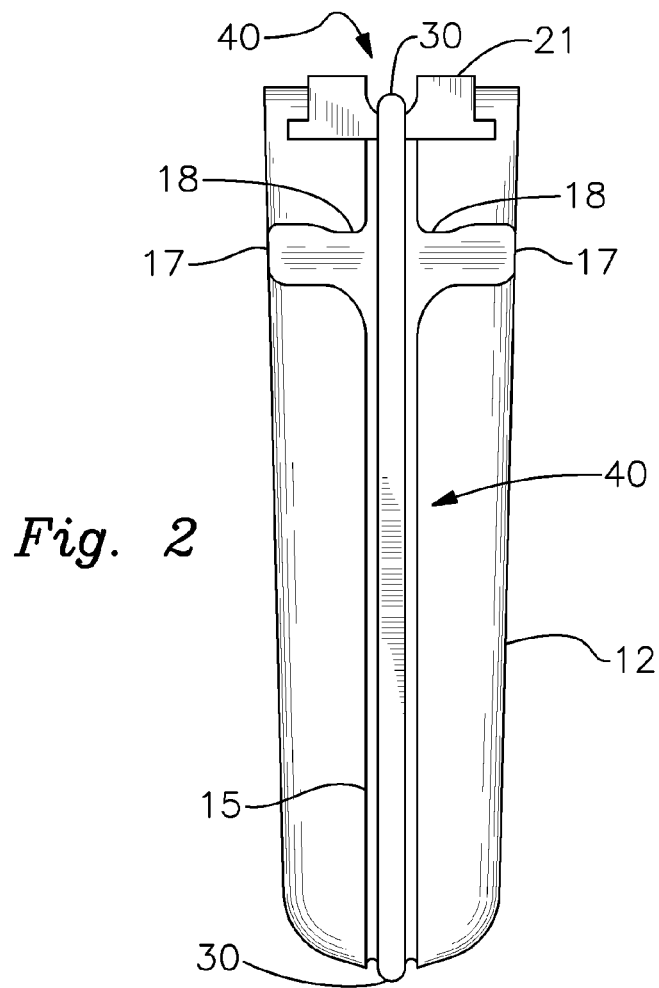
FIG. 2 is an end view of the embodiment of FIG. 1, shown with a suture in place.
Figure 3:
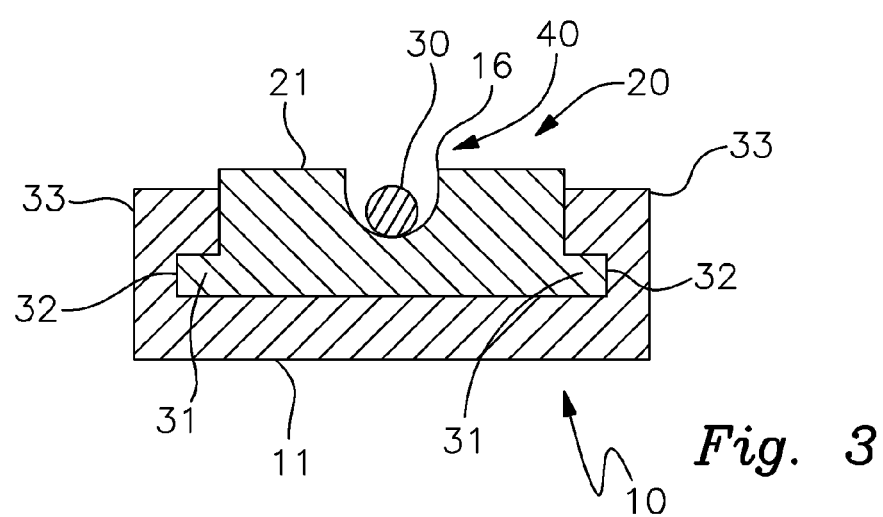
FIG. 3 is a cross-sectional view of the embodiment of FIG. 1, taken along line III-III, shown with a suture in place in the bridging channel.

Preferably, the sternal clamp further comprises anchoring channels 17/27 extending generally laterally on the exterior sides of the projection members 12/22, the anchoring channels 17/27 communicating with the projection channels 15/25 as shown in FIGS. 1 and 2. In this manner, the anchoring channels 17/27 define anchoring cleats or shoulders 18/28 that may be utilized to facilitate the tying of the suture 30 or to better secure the suture 30.

It is understood that equivalents or substitutions for certain elements set forth above may be obvious to those of ordinary skill in the art, and therefore the true scope and definition of the invention is to be as set forth in the following claims. Furthermore, the examples or embodiments set forth above are not meant to be limiting.

I claim:

1. A sternal clamp comprising:
a first sliding body member and a second sliding body member mated in telescoping manner,
a suture-receiving channel disposed on the exterior of each of said first sliding body member and said second sliding body member,
laterally extending anchoring channels disposed on each of said first and said second sliding body members, said anchoring channels communicating with said suture-receiving channel,
anchoring cleats disposed on each of said first and said second sliding body members, said anchoring cleats defined by the combination of said suture-receiving channel and said anchoring channels, and
a suture member encircling said first sliding body member and said second sliding body member, said suture member disposed in said suture-receiving channel;
whereby said first sliding body member and said second sliding body member are securable in a compressed position by said suture member.

2. The clamp of claim 1, said first and said second sliding body member each comprising an interconnecting bridging portion;
wherein said suture-receiving channel comprises a longitudinally extending bridging channel disposed on the exterior of one of said interconnecting bridging portions of said first or said second sliding body members.

3. The clamp of claim 2, each of said first and said second sliding body members comprising a projection member, each said projection member adapted to abut a sternum, wherein said suture-receiving channel comprises a projection channel disposed on each of said projection members.

4. The clamp of claim 3, wherein said first and said second sliding body members are free sliding in either direction when not secured by said suture.

5. The clamp of claim 2, wherein one of said interconnecting bridging portions comprises a pair of longitudinally extending rails and the other of said interconnecting bridge portions comprises a pair of elongated slots disposed in longitudinally extending walls, wherein said rails are received within said slots.

6. The clamp of claim 5, wherein said first and said second sliding body members are free sliding in either direction when not secured by said suture.

7. The clamp of claim 2, wherein said first and said second sliding body members are free sliding in either direction when not secured by said suture.

8. The clamp of claim 1, each of said first and said second sliding body members comprising a projection member, each said projection member adapted to abut a sternum, wherein said suture-receiving channel comprises a projection channel disposed on each of said projection members.

9. The clamp of claim 8, wherein said first and said second sliding body members are free sliding in either direction when not secured by said suture.

10. The clamp of claim 1, wherein said first and said second sliding body members are free sliding in either direction when not secured by said suture.

11. A sternal clamp comprising:
a first sliding body member and a second sliding body member mated in telescoping manner, each of said first and said second sliding body members comprising a projection member;
a suture-receiving channel disposed on the exterior of each of said projection members,
laterally extending anchoring channels disposed on each of said first and said second sliding body members, said anchoring channels communicating with said suture-receiving channel,
anchoring cleats disposed on each of said first and said second sliding body members, said anchoring cleats defined by the combination of said suture-receiving channel and said anchoring channels, and
a suture member encircling said first sliding body member and said second sliding body member, said suture member disposed in said suture-receiving channel.

12. The clamp of claim 11, each of said first and said second sliding body members further comprising an interconnecting bridging portion;
wherein said suture-receiving channel further comprises a longitudinally extending bridging channel disposed on the exterior of one of said interconnecting bridging portions of said first or said second sliding body members.

13. The clamp of claim 12, wherein one of said interconnecting bridging portions comprises a pair of longitudinally extending rails and the other of said interconnecting bridge portions comprises a pair of elongated slots disposed in longitudinally extending walls, wherein said rails are received within said slots.

14. The clamp of claim 13, wherein said first and said second sliding body members are free sliding in either direction when not secured by said suture.

15. The clamp of claim 12, wherein said first and said second sliding body members are free sliding in either direction when not secured by said suture.

16. The clamp of claim 11, wherein said first and said second sliding body members are free sliding in either direction when not secured by said suture.

\* \* \* \* \*